US00PP13860P29

(12) United States Plant Patent
Meilland

(10) Patent No.: US PP13,860 P2
(45) Date of Patent: Jun. 3, 2003

(54) HYBRID TEA ROSE PLANT NAMED 'MEIBACUS'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 28 days.

(21) Appl. No.: 10/021,021

(22) Filed: Dec. 19, 2001

(51) Int. Cl.[7] ..... A01H 5/00
(52) U.S. Cl. ..... Plt./137
(58) Field of Search ..... Plt./137

*Primary Examiner*—Bruce R. Campell
*Assistant Examiner*—W C Haas
(74) *Attorney, Agent, or Firm*—Burns, Doane, Swecker & Mathis, LLP

(57) ABSTRACT

A new and distinct variety of Hybrid Tea rose plant is provided which abundantly forms attractive very double pink blossoms with intense fragrance. The plant exhibits a semi-erect growth habit, dense dark green foliage with a dull aspect, and good resistance to *Marsonina rosae* and *Sphaeroteca panosa*. The attractive dark green foliage contrasts nicely with the pink blossom coloration. The new variety is particularly well suited for growing as attractive ornamentation in parks and gardens.

1 Drawing Sheet

BOTANICAL CLASSIFICATION

*Rosa hybrida.*

SUMMARY OF THE INVENTION

Figures 1, 2, 3, 4, 5, 6, 7, 8, 9, 10, 11, 12, 13, 14, 15, 16, 17:
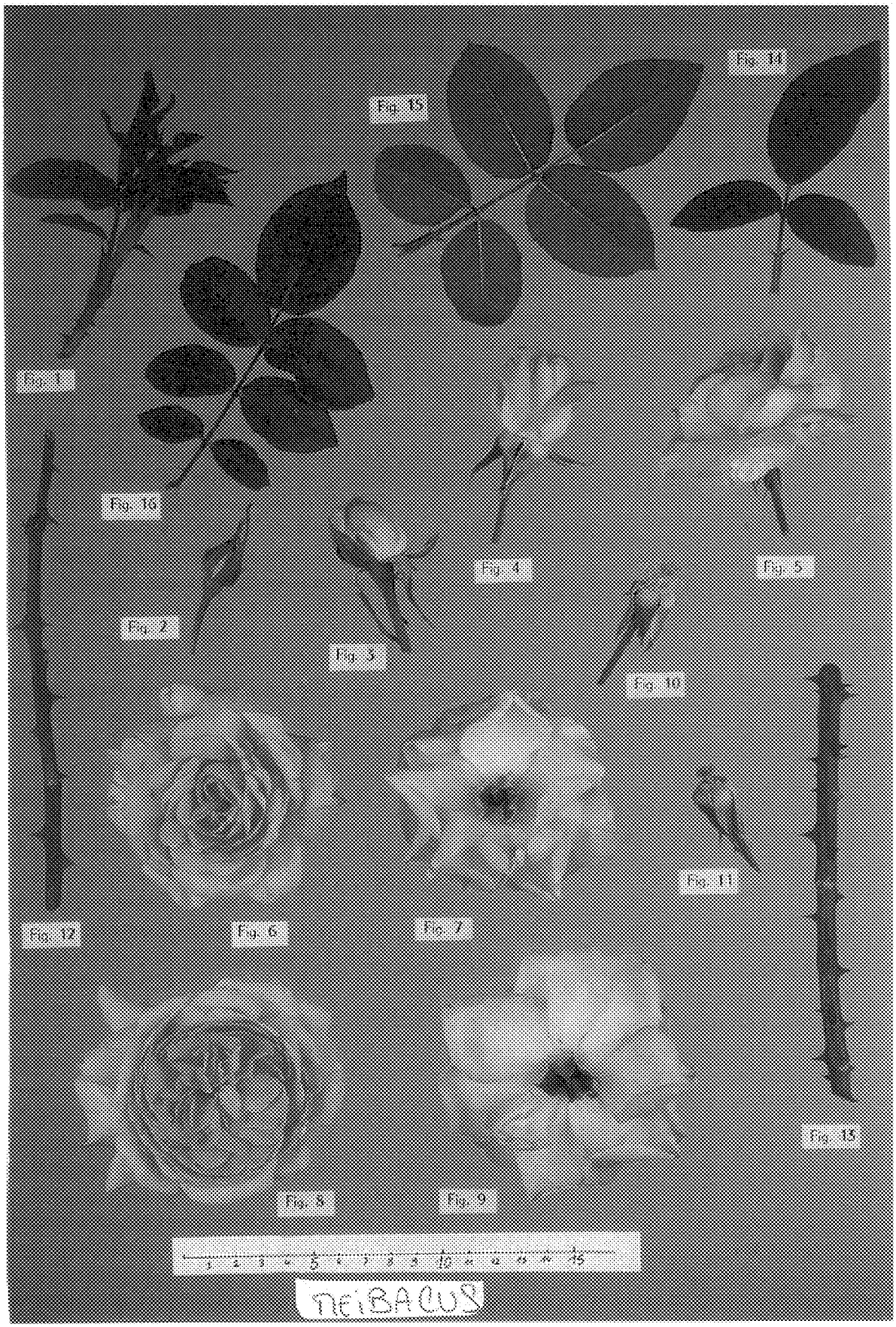

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Delge' variety (non-patented in the United States) and the 'Duc de Windsor' variety (non-patented in the United States). The male parent (i.e., the pollen parent) was the 'Meinimo' variety (U.S. Plant Pat. No. 8,390). The parentage of the new variety can be summarized as follows:

('Delge'×'Duc de Windsor')×'Meinimo'.

The seeds resulting from the above pollination were sown and small plants were obtained which were physically and biologically different from each other. Selective study resulted in the identification of a single plant of the new variety.

It was found that the new variety of the present invention.

(a) exhibits a semi-erect growth habit, (b) abundantly forms on a continuous basis very double pink blossoms with intense fragrance, (c) forms dense dark green foliage with a dull aspect that contrasts well with the pink blossom coloration, and (d) is particularly well suited for growing as attractive ornamentation in parks and gardens.

The disease resistance is good with respect to *Marsonina rosae* and *Sphaeroteca panosa*.

The new variety will meet the needs of the horticultural industry and can be grown to advantage in the landscape where attractive ornamentation is desired.

The new variety can be readily distinguished from its ancestors. For instance, the 'Delge' variety exhibits a dissimilar erect growth habit, the 'Duc de Windsor' variety forms a taller plant with less dense foliage, and the 'Meinimo' variety forms lighter colored blossoms.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meibacus' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately 18 months of age and were observed during June while budded on *Rosa froebelli* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of eighteen month-old plants during June while budded on *Rosa froebelli* understock and growing in greenhouses at Le Cannet des Maures, Var, France.

Class: Hybrid Tea.

Plant:

*Height.*—Approximately 60 to 80 cm on average at the end of the growing season.

*Width.*—approximately 60 to 70 cm on average at the end of the growing season.

*Habit.*—Semi-erect.

Branches:

*Color.*—Young stems: near Yellow-Green Group 148C suffused with Red-Purple Group 60B. Adult wood: near Yellow-Green Group 148B.

*Thorns.*—Size: variable (as illustrated). Quantity: on 10 cm of young stems approximately 6 on average more than 5 mm in length and approximately 12 on average less than 5 mm in length, and on 10 mm of adult stems approximately 10 on average more than 5 mm in length and 8 on average less than 5 mm in length. Color: near Greyed-Red Group 178C on young stems and on adult wood. Configuration: relatively elongated and curved downwards on the upper surface and concave under surface.

Leaves:

*Stipules.*—Adnate, pectinate, rather broad.

*Petioles.*—Upper surface: non-glandular, and near Green Group 139A. Under surface: smooth, and near Yellow-Green Group 146A. Length: approximately 4 mm with terminal leaflet.

*Leaflets.*—Number: 3, 5, and 7 (most often). Shape: somewhat ovate with a rounded base and a cuspidate tip (as illustrated). Size: the terminal leaflets commonly are approximately 6 cm in length and approximately 4 cm in width on average. Serration: simple, fine, and regular (as illustrated). Texture: leathery. General appearance: dense, and dark green with a dull aspect. Color (young foliage): Upper surface: near Green Group 138A suffused with Greyed-Red Group 178A. Under surface: Yellow-Green Group 147C suffused with Greyed-Red Group 178C. Color (adult foliage): Upper surface: near Green Group 139A. Under surface: near Yellow-Green Group 146A.

Inflorescence:

*Number of flowers.*—Commonly one to three per stem.

*Peduncle.*—With tiny prickles, near Red-Purple Group 60B in coloration, and the length is approximately 6 cm on average.

*Sepals.*—Upper surface: tomentose and near Yellow-Green Group 147C in coloration. Under surface: slightly glandular and near Yellow-Green 147C and suffused with Red-Purple Group 60B in coloration. Configuration: elongated with a few extensions (as illustrated).

*Buds.*—Shape: conical. Size: medium (as illustrated). Length: approximately 2 cm on average. Color: Upper surface: near Red Group 39B suffused with Red Group 47 as the calyx breaks. under surface: near Yellow Group 4B suffused with Red Group 52B more or less at the margin as the calyx breaks. Basal petal spot: near Green-Yellow Group 1A on the upper surface and near Green-Yellow Group 1C on the under surface.

*Flower.*—Shape: flat cup-shaped. Diameter: approximately 11 to 12 cm on average. Color (when blooming): upper surface: near Red Group 36D suffused with Red-Purple Group 68B. under surface: near Red Group 36D suffused with Red-Purple Group 68C. Basal petal spot: near Green-Yellow Group 1A on the upper surface and near Green-Yellow Group 1C on the under surface. Fragrance: intense and resembles somewhat that of a ripe peach. Lasting quality: the blossoms commonly last approximately 10 days on the plant average. Petal number: approximately 80 on average under normal growing conditions. Petal shape: commonly undulated and with reflexed edges when fully open. Petal arrangement: imbricated. Petal drop: good with the petals commonly detaching cleanly. Stamen number: approximately 108 on average. Anthers: regularly arranged around the styles and near Yellow-Orange Group 14C in coloration. Pollen: present and yellow in coloration. Filaments: near Yellow-Orange Group 14D in coloration. Pistils: approximately 81 on average. Stigmas: near Yellow-Orange Group 21D. Styles: near Yellow Group 4D in coloration. Receptacle: with some small prickles, near Yellow-Green Group 146B suffused with Red-Purple Group 60B in coloration, and funnel-shaped in longitudinal section. Hips: smooth and rounded and near Yellow-Green Group 144A and 144B in coloration.

Development:

*Vegetation.*—Strong.

*Blooming.*—Very abundant and continuous.

*Resistance to diseases.*—Good with respect to *Marsonina rosae* and *Sphaeroteca panosa.*

*Aptitude to bear fruit.*—Good.

I claim:

1. A new and distinct variety of Hybrid Tea rose plant characterized by the following combination of characteristics:

(a) exhibits semi-erect growth habit, (b) abundantly forms on a continuous basis very double pink blossoms with intense fragrance, (c) forms dense dark green foliage with a dull aspect that contrasts well with the pink blossom coloration, and (d) is particularly well suited for growing as attractive ornamentation in parks and gardens;

substantially as herein shown and described.

* * * * *

NEIBACUS